(12) United States Patent
Drapeau et al.

(10) Patent No.: US 8,153,112 B2
(45) Date of Patent: Apr. 10, 2012

(54) COMPOSITIONS AND METHODS FOR TREATING CAVITY CONDITIONS

(75) Inventors: Susan J. Drapeau, Cordova, TN (US); Josée Roy, Memphis, TN (US); Daniel Andrew Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1074 days.

(21) Appl. No.: 11/890,154

(22) Filed: Aug. 3, 2007

(65) Prior Publication Data

US 2009/0035250 A1   Feb. 5, 2009

(51) Int. Cl.
*A61K 31/00*   (2006.01)
(52) U.S. Cl. ........ 424/78.3; 424/422; 424/426; 424/682
(58) Field of Classification Search ............... 424/78.31, 424/682, 422, 426
See application file for complete search history.

(56) References Cited

U.S. PATENT DOCUMENTS

| | | | |
|---|---|---|---|
| 3,026,248 A | 3/1962 | Noseworthy et al. | |
| 4,020,162 A | 4/1977 | Ghilardi et al. | |
| 4,451,447 A | 5/1984 | Kaplan et al. | |
| 5,605,687 A | 2/1997 | Lee et al. | |
| 6,800,298 B1 * | 10/2004 | Burdick et al. | 424/489 |
| 2003/0180364 A1 * | 9/2003 | Chen et al. | 424/486 |
| 2003/0203030 A1 | 10/2003 | Ashton et al. | |
| 2006/0263355 A1 | 11/2006 | Quan et al. | |

FOREIGN PATENT DOCUMENTS

| | | |
|---|---|---|
| GB | 1250304 A | 10/1971 |
| GB | 1286351 A | 8/1972 |
| WO | WO01/28544 A | 4/2001 |
| WO | WO2006/017456 A2 | 2/2006 |
| WO | WO2006/105161 A2 | 10/2006 |

OTHER PUBLICATIONS

Kaptanoglu et al., "Effects of magnesium sulphate in experimental spinal cord injury: evaluation with ultrastructural findings and early clinical results," Journal of Clinical Neuroscience (2003); vol. 10, No. 3, pp. 329-334.
Borgens R E and Bohnert D., "Rapid recovery from spinal cord injury after subcutaneously administered polyetheylene glycol," Journal of Neuroscience Research (2001); vol. 66, pp. 1179-1186.
Ditor D S et al., "Effects of polyethylene glycol and magnesium sulfate administration on cinically relevant neurological outcomes after spinal cord injury in the rat," Journal of Neuroscience Research (2007); vol. 85, pp. 1458-1467.
The International Search Report and The Written Opinion of the International Searching Authority in PCT/US2007/067580, (2007).
Bondok et al., "Intra-articular magnesium is effective for postoperative analgesia in arthroscopic knee surgery," Br. J. Anaesth., Sep. 2006; 97(3): 389-92, (2006).
Koining et al., "Magnesium sulfate reduces intra- and postoperative anagelsic requirements," Anesth. Analg., Jul. 1998; 87(1):206-10, (1998).
Hedberg et al., "Controlled release of hyaluronan oligomers from biodegradable polymeric microparticle carriers," J. Control Release, Nov. 24, 2004; 100(2): 257-66, (2004).
Bolcal et al., "Comparison of magnesium sulfate with opioid and NSAIDs on postoperative pain management after coronary artery bypass surgery," J Cardiothorac Vasc Anesth., Dec. 2005; 19(6):714-8, (2005).
Crosby et al., "The safety and efficacy of a single dose (500mg or 1g) of intravenous magnesium suflate in neuropathic pain poorly responsive to strong opioid analgesics in patients with cancer," J Pain Symptom Manage., Jan. 2000; 19(1):35-9, (2000).
Hauet et al., "Protective effect of polyethylene glycol against prolonged cold ischemia and reperfusion injury: study in the isolated perfused rat kidney," J Pharmacol Exp Ther., Jun. 2001; 297(3):946-52, (2001).
Phillips et al., The use of a non-ionic surfactant (P188) to save chondrocytes from necrosis following impact loading of strong opioid analgesics in patients with cancer, J Pain Symptom Manage., Jan. 2000; 19(1):35-9, (2000).
Shi et al., "Functional reconnection of severed mammalian spinal cord axons with polyethylene glycol,"; J Neurotrauma., Aug. 1999: 16(8):727-38, (1999).
Shi et al., "Acute repair of crushed guinea pig spinal cord by polyethylene glycol,"; J Neurophysiol., May 1999; 81(5):2406-14, (1999).
McCartney et al., "A qualitative systematic review of the role of N-Methyl-D-aspartate receptor antagonists in preventive analgesia,"; Anesth. Analg. 2004; 98:1385-400, (2004).

* cited by examiner

*Primary Examiner* — Jeffrey S. Lundgren
*Assistant Examiner* — Ibrahim D Bori

(57) ABSTRACT

Compositions, methods and kits to be used as a lubricant and for treatment of a cavity pathology including joint pathology are provided. The composition comprises therapeutically effective amounts of at least one bioactive agent, such as magnesium compound, at least one lubricating agent, such as hyaluronic acid, and at least one cell membrane repairing agent, such as polyethylene glycol. The components of these compositions may be administered by a direct application, an application through a cannula, an intra-articular injection, as a flush fluid during an arthroscopy of the affected area, as a post-arthroscopy injection, or as part of a lavage of the area affected by the intra-articular pathology. In addition, the composition of the present invention may be administered to the patient from a pump or a depot.

21 Claims, No Drawings

COMPOSITIONS AND METHODS FOR TREATING CAVITY CONDITIONS

FIELD OF THE INVENTION

This invention relates to compositions, methods, and kits for treatment of acute and chronic cavity pathology derived from injury, invasive interventions, or degenerative or autoimmune diseases.

BACKGROUND OF THE INVENTION

Within a joint cavity, cartilage is the smooth lining that covers the ends of bones where the bones meet to form the joint and that gives the joint freedom of movement by decreasing friction. The cartilage is kept slippery by synovial fluid, joint fluid made by the joint lining (the synovial membrane). The synovial fluid is contained in a soft tissue enclosure around the joints, called the joint capsule. The synovial fluid has a high content of hyaluronic acid (HA) which increases the viscosity of the synovial fluid. Normal synovial fluid contains 3-4 mg/ml of HA. Along with lubricin, HA is one main lubricating components of the synovial fluid.

If the articular cartilage degenerates or erodes, the concentration of HA decreases and the synovial fluid becomes less viscous. The underlying bone becomes uncovered resulting in bone-to-bone contact which causes significant pain. Additionally, as a result of this bone-to-bone contact, small outgrowths called bone spurs, or osteophytes, may form in the joint. Bits of bone or cartilage can break off and float inside the joint space causing more pain and damage.

Many factors may contribute to the development of a cavity or joint condition. They may include a prior injury to a component of the cavity including strains, rupture, dissection, partial and full tears of the lumen or lining of the cavity, ligaments, tendon, cartilages, meniscus or synovial lining. The cavity or joint may also be affected by an autoimmune disease such as a rheumatoid arthritis or a degenerative disease such as an osteoarthritis (OA).

Currently, there are no effective alternatives for treating joint diseases between a temporary pain relief and a surgical intervention. For example, OA affects approximately 21 million Americans a year accounting for 25% of visits to primary care physicians. It is estimated that 80% of the population will have radiographic evidence of OA by age 65 with more than 60% of those exhibiting symptoms. Most people with osteoarthritis use drug therapy to ease the symptoms of the disease. Majority of OA drugs focus mainly on relieving pain, and have little to no effect on slowing or reversing the breakdown of the cartilage. Another approach to treating osteoarthritis, specifically knee osteoarthritis, is an injection into the joint of hylauronic acid ("HA"). Similar to drug therapies, the HA injections provide temporary relief but do not effect the progression of the disease. Finally, if the above methods of OA management are ineffective, a surgical intervention such as total joint replacement is required.

Co-pending U.S. patent application Ser. No. 11/418,153 discloses compositions comprising PEG and magnesium for treatment of pain or inflammation in subjects. Co-pending U.S. patent application Ser. No. 11/418,152 discloses compositions comprising PEG and magnesium for treatment of neuronal injury in subjects.

Accordingly, there is a need for an effective therapy that will control or more preferably reverse the progression of a cavity pathology in addition to relieving pain.

SUMMARY OF THE INVENTION

The present invention fulfills the foregoing need by providing compositions, methods, and medical kits for treatment of cavity pathology. In one aspect, a therapeutic composition comprising at least one bioactive agent, at least one cell membrane repairing agent, and at least one lubricating agent is provided.

In some embodiments, the bioactive agent comprises a magnesium compound. The at least one cell membrane repairing agent may comprise polyethylene glycol and the lubricating agent may comprise a hyaluronic acid.

In another aspect, a medical kit comprising at least one bioactive agent, at least one cell membrane repairing agent, and at least one lubricating agent is provided. The medical kit may also include a set of instructions comprising information on making a composition for treating a cavity pathology.

In yet another aspect, a method is provided for treating an area affected by a cavity pathology comprising administering to the affected area therapeutically effective amounts of at least one bioactive agent, at least one cell membrane repairing agent, and at least one lubricating agent. The cavity pathology may be caused by a degenerative disease, an autoimmune disease, an injury, invasive medical procedure, or by lack of natural lubricants.

The at least one bioactive agent, at least one cell membrane repairing agent, and at least one lubricating agent may be administered by a joint injection, as a flush fluid during an arthroscopy of the affected area, as a post-arthroscopy injection, or as part of a lavage of the area affected by the joint pathology.

The compositions may be administered by a direct application, by an injection, delivered from a pump, or it may delivered from a preformed device such as a depot for controlled delivery, or any combination thereof.

DETAILED DESCRIPTION

Therapeutic compositions for treating a cavity pathology comprising a bioactive agent, and either a cell membrane repairing agent, a lubricating agent or combination thereof are provided. The Applicants have unexpectedly discovered that such compositions are useful to minimize or reverse the effects of cavity pathology.

The term "cavity" is defined as a space within a biological structure that can be filled by a gas or fluid. Examples of cavity would include lumen or tubular cavities such as for example intestinal, digestive, respiratory and ear cavities; socket cavities including orbital, cranial, pleural, pericardial and sinus cavities as well as joint cavities composed of a space between two or more bones.

The term "cavity pathology" includes pathology affecting cavities including tubular, socket and joint cavities such as articulating joints, fibrous joints, and cartilaginous joints. Variety of cavities may be affected by acute or chronic cavity pathology including, but are not limited to, spinal disc; synovial joint such as elbows, wrist, finger, hip, knee, ankle, toe; fibrous and cartilaginous joints such as skull, pelvis, spinous processes and vertebrae, spine, ribs and clavicle.

It may be caused by an autoimmune disease, rheumatoid arthritis, degenerative disease, temporomandibular joint disorder, injury, trauma such as full and partial tears, ruptures, sprains, dissections; medical intervention, surgery, inflammation, defects, need for additional lubricants, or combinations thereof. Factors that may influence the development of a chronic cavity pathology may include, but are not limited to, a prior injury to a component of the cavity such as strains, rupture, dissection, partial and full tears of the lining of the cavity, ligament, tendon, cartilages, meniscus or synovial lining.

Specific examples of cavity pathologies include, but are not limited to, degenerative diseases of the joint such osteoarthritis; autoimmune diseases of the joint such as rheumatoid arthritis; acute injury of the joint, ligament inflammation, ligament strains, ligament rupture, ligament dissection, ligament partial and full tears, tendon inflammation, tendon strains, tendon rupture, tendon dissection, tendon partial and full tears, synovial lining strains, synovial lining ruptures, synovial lining partial and full tears, cartilage (condyle, patella, trochlea), OCD lesions, osteochondral defects, chondral defects, meniscus inflammation, meniscus strains, meniscus rupture, meniscus dissection, meniscus partial and full tears, degenerative diseases of the temporomandibular joint ("TMJ"), acute injury of the TMJ, degenerative diseases of the spinal disc, acute injury of the spinal disc, degenerative diseases of articulating or synovial joints, acute injury of articulating joints such as shoulder, elbow, wrist, finger, hip, knee, ankle, toe; TMJ degenerative diseases of fibrous or cartilaginous joints, acute injury of fibrous or cartilaginous joints such as skull, pelvis, spinous processes and vertebrae, spine, ribs, and clavicle.

A term "bioactive agent" refers to a compound or molecule that effects or stimulates a living cell. The bioactive agents may be selected from such broad categories as, for example, disease-modifying agents, neurotransmitter, neuropeptides and neuronal receptor modulators, anti-inflammatory and immunomodulator agents, antioxidants, anti-apoptotic agents; nootropic and growth agents, modulators of lipid formation and transport, modulators of blood flow and vessel formation, analgesics, steroidal anti-inflammatory drugs such as corticosteroids, non-steroidal anti-inflammatory drugs such as salicylates, COX-2 inhibitors, TNFα inhibitors, opiates and morphinomimetics, among others.

Additionally, the bioactive agent may comprise drugs which are used in many autoimmune disorders to slow down OA disease progression. Some examples of such drugs include, but are not limited to, adalimumab, azathioprine, chloroquine, etanercept, infliximab, leflunomide, methotrexate, sulfasalazine or combinations thereof.

Disease-modifying bioactive agents can either slow the progression of the disease or potentially reverse some or all of the disease characteristics or symptoms. Some examples of such DMOADs include, but are not limited to, MIA CD-RAP, statins, MMP inhibitors, growth factors, diacerein or combinations thereof.

Specific examples of bioactive agents include, but are not limited to, antioxidant agents such as a free radical scavenger, a chelator, an enzyme, a co-enzyme, a spin-trap agent, a lipid peroxidation inhibitor; agents that can modulate neurotransmitter release and receptor such as glutamate, opioids, ATP-dependent, cannabinoid, adenosine, serotonine, neuropeptide, dopamine, acetylcholine, nicotine, GABA, ion channels, G-protein receptors, voltage-gated and aquaporin channels; anesthetics and anticonvulsants; agents targeting proteins, DNA or RNA synthesis as well as factors that can affect the vascular system including modulators of angiogenesis, coagulation or blood flow modulators, osmotic diuretics and modulators of cellular and/or vascular oedema formation, anti-inflammatory and immunomodulator agents, immunophilins, steroids, analgesics, neurosteroids, cytokines and modulators of cytokine and cytokine receptors including prostaglandins, bradykinin and associated receptors MAO, COX, nitric oxide synthase or phosphodiesterase modulators, agents affecting immune cell activation, adhesion or migration, antiapoptotic strategies such as inhibition of pro-apoptotic signals (caspases, proteases or kinases, death receptors, cytochrome C release, inhibitors of mitochondrial transition pore opening and swelling) or promotion of anti-apoptotic molecules (bcl-2) or cell cycle modulators, nootropic and growth agents such as ATP, glucose, oxygen carriers and growth factors, agents that can block growth inhibitory proteins or proteoglycans, gangliosides, hormones as well as modulators of the cytoskeleton, chaperons and proteolytic pathways as well as agents affecting lipid formation, storage and release pathways such as apolipoprotein, statins and derivates. Other approaches that could beneficiate from this invention include treatment modalities based on electrical stimulation, cell therapy, proteins or peptides, antibodies or nanobodies and other polymer(s) combinations.

In the preferred embodiment, the bioactive agent comprises a magnesium compound. Various magnesium salts may provide a source for the magnesium compounds. Suitable magnesium salts include, but are not limited to, magnesium sulfate, magnesium carbonate, magnesium chloride, magnesium aspartate, magnesium oxide, magnesium stearate, magnesium hydroxide, magnesium trisilicate, magnesium gluconate, magnesium ATP or any combination thereof. These compounds are readily available commercially from, for example, Sigma Aldrich, St. Louis, Mo., USA. Preferably, a Magnesium Chloride is used in a range of between about 0.001 and about 15% weight per volume.

The magnesium compounds have been found to reduce pain in surgical procedures in general (Bolcal et. Al., 2005; Aspan et al., 2004; McCartney et al., 2004), and in arthroscopic knee surgery in particular (Bondok et al., 2006; Koining et al., 1998). It appears, however, that magnesium effect may be of short duration such as 4 hours or less (Crosby et. Al). Thus, it may be advantageous to combine the magnesium compound with materials that will lead to a more sustained impact on symptomatic pain and tissue damages. A combination of the magnesium compound with the cell membrane repairing agents or with the lubricating agents may achieve that objective and may effectively extend the therapeutic effect of magnesium.

The term "cell membrane repairing agent" refers to a compound capable of reversing cell membrane permeabilization. Permeabilization of cell membranes produced by damage or disease leads to cellular death or tissue atrophy (Lee et al. 1992, 1993). For more than 40 years, cell membrane repairing agents of various molecular weights have been utilized as adjuncts to culture media for their ability to protect cells against fluid-mechanical injuries. Cell membrane repairing agents can be effective following different modes of delivery including local and prolonged cellular exposure, direct and short-term tissue or organ exposure or systemic administration. Effective concentrations of cell membrane repairing agents preferably vary from about 0.05 to about 50% weight per volume in some embodiments and from about 0.05 to 90% weight per volume in other embodiments. In yet other embodiments, the concentration of the cell membrane repairing agent is between about 10 and 70 percent weight per volume. Cell membrane repairing agents of various molecular weights and various chemical structures such as PEGs of 400-20000 Da and having a linear or multiple arms structure can improve recovery following tissue injury (Hauet et al., 2001; Detloff et al., 2005, Shi et al., 1999). They were also shown to protect articular cells from secondary injury following mechanical trauma to knee joint which could lead to accute pain and inflammation and potentially develop into osteoarthritis. (Phillips and Hauet, 2004).

The cell membrane repairing agents may be selected from hydrophilic polymers, hydrophobic polymers, amphipatic polymers, or combinations thereof. More specifically, suitable examples of cell membrane repairing agents include, but are not limited to, polyethylene glycol (PEG), a block copolymer containing a polyalkylene glycol, triblock containing a polyethethylene glycol, poloxamer P-188 (also known as CRL-5861, available from CytRx Corp., Los Angeles, Calif.), polyalkylene glycol, a block copolymer containing a polyalkylene oxide, triblock containing a polyalkylene oxide, polyvinyl alcohol, polyvinyl pyrrolidone, dextrans, poloxamine, pluronic polyols, dimethylsulfoxide, starch, hydroxyethylstarch, sodium carboxymethyl cellulose, methyl cellulose, poly(polyethylene glycol methacryalte), poly(glycerol methacrylate), poly(glycerol acrylatete), poly(polyethylene glycol acrylate), poly(alkyl oxazoline), phosphoryl choline polymers, sodium and potassium polymethacrylate, sodium and potassium polyacrylate, polymethacrylatic acid and polyacrylic acid and combinations thereof.

In one embodiment, the cell membrane repairing agent may comprise polyethylene glycol (PEG). Due to its strong safety profile, PEG is used in numerous clinical applications and, thus, is readily available on the market. PEG of different molecular weights may be obtained from, for example, Sigma-Aldrich, St. Louis, Mo., USA. PEG of molecular weights between about 100 and 20000 DA may be used. A more preferred concentration range of PEG is about 1500 to 9000 DA. The concentration of PEG may range from about 0.05% to about 50% weight per volume in some embodiments and from about 0.05 to 90% weight per volume in other embodiments. In yet other embodiments, the concentration of PEG is between about 10 and 70 percent weight per volume. PEG may also compliment the lubricating agent because it possesses favorable viscoelastic properties.

In one embodiment, the composition further comprises an antioxidant. A suitable non-limiting example of the antioxidant is butylated hydroxytoluene (BHT). BHT is produced by the reaction of p-cresol with isobutylene. It was patented in 1947 and received approval of the Food and Drug Administration for use as a food additive and preservative in 1954. BHT is a fat-soluble organic compound primarily used as an antioxidant food additive. It is also used as an antioxidant in cosmetics, pharmaceutical drugs, jet fuels, rubber, petroleum products, and embalming fluid.

BHT reacts with free radicals, slowing the rate of autoxidation in food, cosmetic and pharmaceutical formulations and preventing changes in odor, color or taste. It can be found in injectable pharmaceutical compositions. For the purposes of the instant invention, the composition may contain between about 0.00003 and about 0.3% of BHT (weight/volume), or, in a selected embodiment, between about 0.001 and about 0.03% (weight/volume).

A term "lubricating agent" refers to a compound administered to supplement or replace the viscous properties of the synovial fluid to provide lubrication of the joints. Since, as described above, Hyaluronic Acid ("HA") is a natural component of synovial fluid and plays an essential part in its viscoelastic properties, HA is a natural candidate for a lubricating agent. Another suitable example of the lubricating agent comprises Lubricin which is available from, for example, Affinity BioReagents, Inc. of Golden, Co.

Hyaluronic acid or sodium hyaluronate is a high molecular weight polysaccharide of N-acetyl glucosamine and glucuronic acid molecules that is naturally occurring in all mammals in a variety of tissue and some bacterial species. HA can thus be derived from various animal sources as well as be produced through culture or synthetic assembly methods. For the purposes of this invention, hyaluronic acid includes any derivatives such as hyaluronan and hyaluronic acid itself with $H^+$ ion attached to the $COO^-$ group, and salts of hyaluronic acid whereby another positive ion replaces the $H^+$ ion, as for example, with $Na^+$ which forms sodium hyaluronate. Also included in the definition of hyaluronic acid is any physically or chemically cross-linked hyaluronic acid or derivative. Hyaluronic acid polymers are very large with molecular weights of between about 100 and 90,000,000 DA and can displace a large volume of water. For the purposes of the present invention, a preferred embodiment includes a non-cross linked hyaluronic acid with a molecular weight of 0.5 to 10 M Dalton.

Currently, there are at least five FDA approved HA based products on the market. They include Euflexxa™, Hyalgan®, Synvisc®, Supartz® and Orthovisc®. Any of these products or any combinations thereof may be used as the lubricating agent for the combinations described herein. Although hyaluronic acids from other sources are acceptable, for medical purposes it is preferable to use the ones approved by or known to the FDA. The HA solution can be in a range of about 0.05 and about 50% weight per volume.

The compositions described above may be used to prepare therapeutic formulations. Such formulations may be prepared by mixing the at least one bioactive agent and either at least one cell membrane repairing agent or at least one lubricating agent or any combination thereof with optional physiologically acceptable carriers, excipients or stabilizers (see, e.g., Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenyl, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or metal complexes (e.g., Zn-protein complexes).

The formulations herein may also contain more than one bioactive compound as necessary for the particular indication being treated, preferably those with complementary activities that do not adversely affect each other. Such molecules are suitably present in combination in amounts that are effective for the purpose intended.

The present compositions may also be entrapped in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

Sustained-release preparations including the at least one cell membrane repairing agent or at least one lubricating agent may also be prepared. Suitable examples of sustained-release preparations include semipermeable matrices of solid polymers containing the at least one biomembrane sealing agent and/or the at least one bioactive agent, which matrices are in the form of shaped articles, e.g., films, or microcapsule.

Examples of sustained-release matrices include, without limitations, polyesters, hydrogels (for example, poly(2-hydroxyethyl-methacrylate), or poly(vinylalcohol)), polylactides (see, e.g., U.S. Pat. No. 3,773,919), copolymers of L-glutamic acid and y ethyl-L-glutamate, non-degradable ethylene-vinyl Oacetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. Polymers such as ethylene-vinyl acetate and lactic acid-glycolic acid enable release of molecules for over 100 days.

In another aspect, kits for preparation of compositions described above are provided. Such kits comprise at least one bioactive agent, and at least one cell membrane repairing agent, at least one lubricating agent, or both. The kit may also include a set of instructions. The kit provides a practitioner with an advantageous flexibility in selecting the ratios of the components of the composition.

A preferred kit configuration may include a MgCl solution vial, an HA solution vial, a PEG vial, a sterile saline vial, multiple syringes, a syringe connector, a needle for injection, or radio-opaque dye. The magnesium salt can be provided as a solid or in a solution.

In the preferred embodiment, the MgCl hexahydrate solution may be used in a range of 0.01 and 15 percent weight per volume in sterile fluid, more preferably between 0.01 and 8 percent weight per volume. Between about 0.01 and 10 milliliters of the MgCl solution may be provided. The MgCl solution may be diluted to the desired final concentration. The HA solution may be used at about 0.05 and 50 weight percent per volume, more preferably at about 1 to 3 percent weight per volume in sterile fluid. The concentration may be higher if other components will be added to it, lowering the final concentration. A PEG solution may be used in the range of about 0.05 to 50% weight per volume or in the range of about 0.05 to 90% weight per volume in other embodiments. More preferably, the concentration of PEG is between about 10 and 70 percent weight per volume. Again, the concentration may be higher if other components are be added to it, lowering the final concentration.

A set of instructions is also provided in the kit. The set of instructions preferably includes information necessary for proper use of the kit, such as dosage and timing of administration of the composition of the present invention. Optionally, the set of instructions may also provide secondary information concerning, for example, postoperative care and observations of the patients receiving orthopedic implants coated with the composition of the present invention. A person of ordinary skill in the art will appreciate that the set of instructions can be in any suitable medium, including, without limitation, printed, video-taped, digital, and audio-recorded. In addition to English language instructions, instructions in other languages may be provided.

The medical kit described above provides the surgeon with many of the tools necessary to practice the methods of treating an area affected by an intra-articular pathology. These methods comprise administering to the affected area a composition comprising therapeutically effective amounts of at least one bioactive agent, and either at least one cell membrane repairing agent, at least one lubricating agent, or both.

The term "treating" refers to executing a protocol, which may include administering one or more drugs to a patient (human or otherwise), in an effort to alleviate signs or symptoms of the disease. Alleviation can occur prior to signs or symptoms of disease appearing, as well as after their appearance. Thus, "treating" or "treatment" includes "preventing" or "prevention" of the disease. In addition, "treating" or "treatment" does not require complete alleviation of signs or symptoms, does not require a cure, and specifically includes protocols which have only a marginal effect on the patient.

The term "therapeutically effective amount" means a quantity of an agent which, when administered to a patient or subject, is sufficient to result in an improvement in patient's condition. The improvement may be determined in a variety of ways. Additionally, the improvement does not mean a cure and may include only a marginal change in patient's condition.

At least one bioactive agent, at least one cell membrane repairing agent, and at least one lubricating agent may be delivered independently of each other. Alternatively, these compounds may be pre-mixed before administration. Suitable methods of administration include, but are not limited to, intravenous administration, an intramuscular administration, an intrathecal administration, a subcutaneous administration, an epidural administration, a parenteral administration, an intra-articular administration, a direct application or deposition onto or adjacent to a site of the pathological condition, and any combinations thereof. In the preferred embodiment, the compositions or individual components are delivered by direct intra-articular injection followed by flexion/extension of the joint 10+ times to distribute the fluid.

In addition, the at least one bioactive agent, at least one cell membrane repairing agent, and at least one lubricating agent may be be administered as a flush fluid during an arthroscopy of the affected area, as a post-arthroscopy injection, or as part of a lavage of the area affected by the intra-articular pathology. The concentration of each of the components may vary from the therapeutic formulation to that used for a lavage solution.

In some embodiments, the composition of the present invention may be administered to the patient from a depot. An example of suitable non-limiting design of a depot implant is discussed in details in a co-pending application entitled Drug Depot Implant Designs And Methods Of Implantation, Ser. No. 11/403,733, filed on Apr. 13, 2006, incorporated herein by reference in its entirety.

In other embodiments, the composition as described above may be delivered to the target site using a pump disposed either within or outside a patient. The use of a pump may be preferable when administration of the compositions over a extended period of time is required. One example of a suitable pump is the SynchroMed® pumps (Medtronic, Minneapolis, Minn.) or Alzet® osmotic pumps (Durect Corporation, Cupertino, Calif.). Additional designs which may be adapted to be employed in the method of the present invention are provided, for example, in United States patent applications, such as US 2002/0082583 (a pre-programmable implantable apparatus with a feedback regulated delivery method), US 2004/0106914 (a micro-reservoir osmotic release system for controlled release of chemicals), US 2004/0064088 (a small, light-weight device for delivering liquid medication), US 2004/0082908 (an implantable microminiature infusion device), US 2004/0098113 (an implantable ceramic valve pump assembly), and US 2004/0065615 (an implantable infusion pump with a collapsible fluid chamber), incorporated herein by reference in its entirety. Potential drug delivery devices that may be suitable for use with the pump include, but are not limited to, those devices found in U.S. Pat. Nos. 6,551,290, 6,571,125, 6,594,880, or 5,752,930, incorporated herein by reference in its entirety.

It may be advantageous to use the at least one marker with the implant. The at least one marker may be included on the drug depot implant itself. In this embodiment, a practitioner will be better equipped to accurately position the implant into a tissue of a patient. As discussed above, the at least one marker may be a radiographic marker, such as, for example, barium, calcium phosphate, and metal beads. In another embodiment, the at least one marker may comprise iodine-based contrast agents, such as, for example, iopamidol, commercially available as Isovue™ (Bracco Diagnostics Inc., Princeton, N.J.) or iodixanol, commercially available as Visipaque™ (Nyocomed, Inc., Princeton, N.J.), and gandolinium-based contrast agents, such as, for example, gadodiaminde, commercially available as Omniscan (available from GE Healthcare, Princeton, N.J.). Such markers will also permit the practitioner to track movement and degradation of the implant in the tissue over time. In this embodiment of the invention the practitioner may accurately position the implant in the tissue using any of the numerous diagnostic imaging procedures known to one of ordinary skill in the art. Such diagnostic imaging procedures include for example, X-ray imaging or fluoroscopy.

EXAMPLES

Example 1

Treatment of Injury to the Anterior Cruciate Ligament with Hyaluronic Acid in Combination with Peg and Magnesium Compound Minimized the Signs of Degenerative Joint Disease as Compared to Treatments with Saline or Hyaluronic Acid Alone Test Sample Preparation:

Group 1 and Group 2 were injected with saline and Supartz® provided ready to use by Sponsor respectively. To prepare test article for Group 3, 0.13 mL from container containing 55.4% PEG3350 (weight/vol) and 3.7% MgCl (weight/volume) was drawn into a 1 cc syringe and injected into the Supartz® test article and mixed back and forth ten to fifteen times for a final solution containing 2.74% PEG3350 (weight/volume), 0.18% magnesium chloride hexahydrate (weight/volume) and HA The solution was then mixed 30-50 times in a 6 cc syringe, then 0.3 mL was drawn up.

Experimental Method Summary:

The test was conducted in 4 groups (three test and one control) with 6 rabbits in each group. Animals were anesthetized and prepared for surgery. With sharp and/or blunt dissection, access was created to the correct location in the right knee joint. The anterior cruciate ligament (ACL) was then completely transected under direct visualization. The incisions were closed in accordance with standard surgical techniques. The animals were recovered from anesthesia and returned to their cages. Four weeks post-op, each animal received intra-articular injection treatments of either saline (control, Group 1), Supartz® (Group 2), or Supartz® in combination with PEG and MgCl (Group 3) into the right knee joint. No injections were given to the non-operated left knee. At weekly intervals thereafter out to 8 weeks, all groups received additional weekly injections of their test or control article into the right knee.

TABLE 1

Test Article Distribution and Timing

| Group | Test Article | # of Animals | Time of Injection (weeks post-op) |
|---|---|---|---|
| 1 | Saline control | 6 | 4, 5, 6, 7, 8 |
| 2 | Supartz ® | 6 | 4, 5, 6, 7, 8 |
| 3 | Supartz ® in combination with PEG and MgCl | 6 | 4, 5, 6, 7, 8 |

* Animal #s 8491, 8501, 8505, and 8506 received the last (fifth) injection one day after the other animals in this group.

The animals were in-life for 4 months. Surgical site inspection occurred for evidence of post-surgical wound infection once daily for the first 7 days, and twice weekly thereafter. Animals were observed daily for abnormal clinical signs.

At Week 16 post-op (12 weeks after first injection), the animals were sacrificed. The rabbits were weighed, sedated with a cocktail of butorphanol (1 mg/kg) and acepromazine (1 mg) and then euthanized with a concentrated barbiturate euthanasia solution (Beuthanansia-D) dosed intravenously to effect. The joints were then dissected open and the articular surfaces examined. The area was washed in India ink to aid in visualization of fibrillated cartilage. Digital photographs were taken of the articular surface of the distal femoral condyle. The tissue was then explanted, and fixed and processed for pathology.

Necropsy Observation: At termination, joints were opened and examined, and washed in India ink to aid in visualization of fibrillated cartilage. Digital photographs were taken of the articular surfaces of the distal femoral condyles and opposing tibial plateau. All photographs were sent directly to Sponsor on CD. A written summary of the veterinarian's assessment of the joint at necropsy is presented in Table 2. The abbreviation "AC" in the necropsy notes refers to the articular cartilage of the femoral condyles. Unless noted to the contrary, the left stifle joint (non-operated) was normal.

Osteophyte formation was observed in most animals in all groups. Articular cartilage was described as "good" and/or "smooth" in 0/6 in Group 1, 2/5 in Group 2, and 4/6 in Group 3, as shown in Table 2.

TABLE 2

Tabular Representation of India Ink Observations
(Right side, unless otherwise noted)

| Group | Animal Number | Presence of Osteophytes | Articular Cartilage Fibrillation | Synovial Swelling | Articular Cartilage Roughening | Smooth (Good) Articular Cartilage |
|---|---|---|---|---|---|---|
| 1 | J8485 | X | | | | |
|   | J8487 | X | X | | | |
|   | J8490 | X | X | | | |
|   | J8494 | X | X | | | |
|   | J8495 | X | | | X | |
|   | J8497 | X | | | | |

TABLE 2-continued

Tabular Representation of India Ink Observations
(Right side, unless otherwise noted)

| Group | Animal Number | Presence of Osteophytes | Articular Cartilage Fibrillation | Synovial Swelling | Articular Cartilage Roughening | Smooth (Good) Articular Cartilage |
|---|---|---|---|---|---|---|
| 2 | J8482 | X | | | | |
|   | J8483 | X | | X | | |
|   | J8489 | N.A. | N.A. | N.A. | N.A. | N.A. |
|   | J8492 | X | | | | X |
|   | J8493 | X | | | | X |
|   | J8498 | | | | X | |
| 3 | J8491 | X | | | | X |
|   | J8496 | X | | X | | |
|   | J8501 | X | | | | X |
|   | J8503 | X | | | | X |
|   | J8505 | X | X | X | X | |
|   | J8506 | X | | | | X |

N.A. = not applicable;
animal J8489 was euthanized one month post-op due to unresolved chronic infections and lick granulomas.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A therapeutic composition comprising therapeutically effective amounts of at least one bioactive agent comprising a magnesium compound in the range of about 0.01 to 15% weight to volume; at least one lubricating agent comprising a hyaluronic acid in the range of about 0.05 to 50% weight per volume; at least one cell membrane repairing agent comprising polyethylene glycol (PEG) in the range of about 0.05 to 50% weight to volume; and at least one antioxidant in the range of about 0.00003 to 0.3% weight per volume.

2. The therapeutic composition of claim 1, wherein the composition is used to treat a joint pathology.

3. The therapeutic composition of claim 1 wherein the composition is used to lubricate synovial, fibrous and cartilaginous joints.

4. A method of treating a cavity pathology comprising administering a therapeutically effective amount of therapeutic composition of claim 1 to the affected area.

5. A method of lubricating a joint, comprising administering a therapeutically effective amount of therapeutic composition of claim 1 to the joint.

6. A method of treating a cavity pathology comprising administering to the affected area a composition comprising therapeutically effective amounts of at least one bioactive agent comprising a magnesium compound in the range of about 0.01 to 15% weight to volume; at least one cell membrane repairing agent comprising polyethylene glycol (PEG) in the range of about 0.05 to 50% weight to volume; at least one lubricating agent comprising hyaluronic acid in the range of about 0.05 to 50% weight per volume; and at least one antioxidant in the range of about 0.00003 to 0.3% weight per volume.

7. The method of claim 6, wherein the step of administering the composition comprises administering the composition by a method selected from the group consisting of a direct application, an application through a cannula, intra-articular injection, a lavage of affected area, flush of the affected area, flush fluid during an arthroscopy of the affected area, post-arthroscopy injection of the affected area or combinations thereof.

8. The method of claim 6, wherein the composition is administered from a depot.

9. The method of claim 6, wherein the composition is administered by a pump.

10. The method of claim 6, further comprising the step of delivering at least one marker with the composition.

11. The method of claim 6, wherein the cavity pathology is caused by a disease selected from the group consisting of a degenerative disease, an autoimmune disease, and an acute or chronic condition.

12. The method of claim 6, wherein the cavity pathology is associated with an or acute or chronic condition selected from the group consisting of an injury, an invasive medical intervention, a degenerative disease, and a lack of natural lubricants.

13. The method of claim 6, wherein the cavity pathology affects a joint selected from the group consisting of spinal disc; elbow, wrist, finger, hip, knee, ankle, toe, skull, pelvis, spinous processes, vertebrae, spine, ribs and clavicle.

14. A therapeutic kit comprising at least one bioactive agent comprising a magnesium compound in the range of about 0.01 to 15% weight to volume; at least one cell membrane repairing agent comprising polyethylene glycol (PEG) in the range of about 0.05 to 50% weight to volume; at least one lubricating agent comprising hyaluronic acid in the range of about 0.05 to 50% weight per volume; at least one antioxidant in the range of about 0.00003 to 0.3% weight per volume; and a set of instructions comprising information on making a lubricant composition.

15. The kit of claim 14, wherein the at least one cell membrane repairing agent comprises PEG.

16. The kit of claim 14, wherein the at least one bioactive agent comprises a magnesium compound.

17. The kit of claim 14, wherein the at least one lubricating agent comprises a hyaluronic acid.

18. The kit of claim 14, wherein the set of instructions comprises information on preparing a direct application, an application through a cannula, an intra-articular injection, solution for a lavage of the area affected by the joint pathology, a flush fluid for use during an arthroscopic surgery, a post-arthroscopy injection, or combinations thereof.

19. The therapeutic composition of claim 1, wherein the at least one antioxidant is in the range of about 0.001 to 0.03% weight per volume.

20. The method of claim 6, wherein the at least one antioxidant is in the range of about 0.001 to 0.03% weight per volume.

21. The kit of claim 14, wherein the at least one antioxidant is in the range of about 0.001 to 0.03% weight per volume.

* * * * *